United States Patent [19]

Dockner et al.

[11] Patent Number: 5,734,074
[45] Date of Patent: Mar. 31, 1998

[54] CONTINUOUS PREPARATION OF ALKYL ESTERS OF (METH) ACRYLIC ACID

[75] Inventors: Toni Dockner, Meckenheim; Herbert Exner, Waldsee; Karl Gerhard Baur, Ludwigshafen; Christiane Potthoff, Dortmund, all of Germany

[73] Assignee: BASF Aktiengesellschaft, Ludwigshafen, Germany

[21] Appl. No.: 618,817

[22] Filed: Mar. 20, 1996

[30] Foreign Application Priority Data

Mar. 24, 1995 [DE] Germany ............ 195 10 891.4

[51] Int. Cl.$^6$ .................................. C07C 69/52
[52] U.S. Cl. .................................. 560/205
[58] Field of Search ........................... 560/205

[56] References Cited

FOREIGN PATENT DOCUMENTS

| 14 68 932 | 12/1968 | Germany. |
|---|---|---|
| 2 226 829 | 12/1973 | Germany. |
| 2 252 334 | 5/1974 | Germany. |
| 25 52 987 | 6/1977 | Germany. |
| 25 52 987 | 9/1983 | Germany. |
| 1017522 | 1/1966 | United Kingdom. |
| 1173118 | 12/1969 | United Kingdom. |

*Primary Examiner*—Paul J. Killos
*Attorney, Agent, or Firm*—Oblon, Spivak, McClelland, Maier & Neustadt, P.C.

[57] ABSTRACT

The continuous esterification of a $C_1$–$C_8$-alkanol with (meth)acrylic acid in a molar ratio of from 1:1 to 2:1 in the presence of proton-donating catalysts in a homogeneous, liquid, solvent-free phase, in which the water of reaction and resulting alkyl (meth)acrylate are separated off continuously as part of an aqueous azeotropic mixture via the top of a rectification zone attached to the reaction zone, at a top pressure of from 0.1 to 1 atm, and worked up to give pure (meth)acrylate, is carried out by a process wherein the reaction temperature is from 100° to 150° C., the residence time is from 1 to 5 hours and from 5 to 20% by weight, based on the amount of reaction mixture, of sulfuric acid or an equimolar amount, based on such an amount of sulfuric acid, of an organic sulfonic acid is added as a protic acid catalyst to the reaction mixture present in the reaction zone.

16 Claims, No Drawings

CONTINUOUS PREPARATION OF ALKYL ESTERS OF (METH) ACRYLIC ACID

The present invention relates to a process for the continuous preparation of alkyl esters of (meth)acrylic acid by reacting (meth)acrylic acid and a monohydric alkanol of 1 to 8 carbon atoms in a homongeneous, liquid, solvent-free phase in a molar ratio of from 1 (alkanol):1 ((meth)acrylic acid) to 2 (alkanol):1 ((meth)acrylic acid) at elevated temperatures and in the presence of sulfuric acid or of an organic sulfonic acid as catalyst, in which the (meth)acrylic acid, the alkanol and the acid catalyst are fed continuously to a reaction zone, after a residence time of a few hours the resulting alkyl (meth)acrylate is separated off by rectification, as part of at least one azeotropic mixture consisting of water or water and starting alkanol as further components in addition to the alkyl (meth)acrylate, via the top of a rectification zone attached to the reaction zone and having a top pressure of from 0.1 to 1 atm, the distillate obtained is separated into at least one organic phase containing the alkyl (meth)acrylate and into at least one aqueous phase containing water, some of said organic phase is recycled to the rectification zone via the top and, if required, water is recycled to the reaction zone, the alkyl (meth)acrylate is separated off in a manner known per se from the excess organic phase containing the alkyl (meth)acrylate and some of the reaction mixture is discharged continuously from the reaction zone.

Here (meth)acrylic acid means acrylic or methacrylic acid. Alkyl esters of (meth)acrylic acid are generally known and are, for example, important as starting monomers for the preparation of aqueous polymer emulsions which are used, for example, as adhesives.

Processes for the preparation of alkyl (meth)acrylates by reacting (meth)acrylic acid with monohydric alkanols of 1 to 8 carbon atoms in homogeneous liquid phase at elevated temperatures and in the presence of proton-donating catalysts are known and are described, for example, in DE-A 1468932, 2226829 and 2252334. These are typical equilibrium reactions in which the degree of conversion of the (meth)acrylic acid and of the particular alkanol to the corresponding ester is significantly limited by the equilibrium constant. Consequently, in order to carry out the process economically, the unconverted starting materials must be separated from the ester formed and must be recycled to the reaction zone. As a rule, separation of the ester formed from unconverted (meth)acrylic acid proves to be particularly difficult since their boiling points are generally relatively close together.

Various measures have therefore been proposed for increasing the conversion of the (meth)acrylic acid to the corresponding esters, for example the use of a greater molar excess of alkanol relative to the (meth)acrylic acid, the removal of the water of reaction by means of an organic entraining agent forming a suitable azeotropic mixture or the extraction of the resulting ester with a suitable solvent during the reaction. However, these processes have the disadvantage that a large excess of alkanol has to be removed or the entraining agent or the extracting agent must be isolated. In addition, a large excess of alkanol promotes the formation of its dialkyl ether as a byproduct.

It is now known that the difference between the boiling point of unconverted (meth)acrylic acid and that of the resulting alkyl ester of (meth)acrylic acid can be increased by incorporating the resulting alkyl ester of (meth)acrylic acid in at least one low-boiling aqueous azeotropic mixture which may also contain starting alcohol in addition to the alkyl (meth)acrylate and water, and continuously removing the alkyl (meth)acrylate as a component of at least one such azeotropic mixture by rectification from the reaction zone containing the unconverted (meth)acrylic acid and thus separating it from unconverted (meth)acrylic acid. When the above procedure is carried out continuously, the aqueous azeotropic mixture obtained as a distillate is separated into at least one organic phase containing the alkyl (meth)acrylate and into at least one aqueous phase containing water. Some of the organic phase containing the alkyl (meth)acrylate is recycled via the top of the mounted rectification column to establish the separation effect based on rectification (rectification reflux ratio). The alkyl (meth)acrylate is separated from the excess organic phase containing the alkyl (meth)acrylate in a manner known per se. In the esterification of lower $C_1$- or $C_2$-alkanols, the water of reaction formed as a byproduct in the course of the esterification is usually sufficient to form the composition of the aqueous azeotropic mixture (suitable aqueous azeotropic compositions are described, for example, by Azeotropic Data-III, Advances in Chemistry Series 116, American Chemical Society, Washington, D.C. (1973)) and is thus simultaneously removed continuously from the esterification equilibrium, as a component of the aqueous azeotropic mixture. However, this is no longer the case with increasing chain length of the alkanol, and in these cases additional water over and above the water of reaction formed in the course of the esterification must therefore be introduced into the reaction zone. In the simplest procedure, this is realized by recycling an appropriate part of the aqueous phase produced in separating the aqueous azeotropic mixture obtained as a distillate to the esterification section. Since water tends to present problems with regard to the conversion in the actual esterification reaction, recycling of the aqueous phase is preferably effected via the top of the mounted rectification zone. If the aqueous azeotropic mixture separated off by rectification via the top of the mounted rectification zone contains starting alkanol as an additional component, said alkanol is separated off in a manner known per se from the excess of organic and aqueous phase which remains after separation of the azeotropic distillate into an organic and an aqueous phase after partial recycling thereof and is recycled to the reaction zone. Since the starting alkanol, as one of the two reactants, participates directly in the esterification, this recycling is preferably effected directly.

GB-1017522 discloses a corresponding process for the separation of n-butyl acrylate. As esterification conditions, GB-1017522 recommends a molar ratio of starting alkanol to starting acid of from 2.3 to 5, a reaction temperature of <100° C. and a content of catalytically active sulfuric or organic sulfonic acid of from <0.05 to <5% by weight, based on the total mass of the reactants. The disadvantages of this procedure are the required large excess of starting alkanol, which promotes the formation of undesirable dialkyl ether, and the fact that the n-butyl acrylate yield, based on the amount of acrylic acid used, is not completely satisfactory under the abovementioned conditions.

German Patent 2,552,987 discloses a process for the continuous preparation of alkyl esters of acrylic acid by reacting acrylic acid and monohydric alkanols of 1 to 4 carbon atoms in a homogenous, liquid, solvent-free phase in a molar ratio of from 1 (alkanol):1 (acrylic acid) to 2 (alkanol):1 (acrylic acid) at elevated temperatures and in the presence of sulfuric acid or of an organic sulfonic acid as catalyst, in which the acrylic acid, the alkanol and the acid catalyst are fed continuously to a reaction zone, after a residence time of a few hours the resulting alkyl acrylate is separated off by rectification, as part of at least one aqueous azeotropic mixture consisting of water or water and starting alkanol as further components in addition to the alkyl acrylate, via the top of a rectification column attached to the reaction zone and having a top pressure of from 0.1 to 1 atm, the distillate I obtained is separated into an organic phase containing the resulting acrylate and into an aqueous phase, some of the organic phase is recycled via the top of the rectification column in order to produce a greater separation effect and, if required, some of the aqueous phase is recycled via the top of the rectification column to maintain the composition of the aqueous azeotropic mixture, the alkyl ester is separated in a manner known per se from the excess organic phase and some of the reaction mixture is discharged from the reaction zone and freed from high boilers by distillation and the resulting distillate II is recycled to the reaction zone.

German Patent 2,552,987 recommends a reaction temperature of from 80° to 130° C. In the embodiments, a temperature of 95° C. is used in all cases. German Patent 2,552,987 recommends a residence time of from 4 to 10 hours. In all embodiments, the residence time is more than 6 hours. German Patent 2,552,987 recommends from 0.1 to 3% by weight of sulfuric acid or from 1 to 8% by weight of organic sulfonic acid, based on the reaction mixture, as the amount of acid catalyst to be used. German Patent 2,552,987 mentions only benzenesulfonic acid and toluenesulfonic acid as suitable organic sulfonic acids. In all embodiments, the amount of acid catalyst used is ≦2.5% by weight, based on the reaction mixture.

The primary object of German Patent 2,552,987 is to avoid undesirable ether formation from starting alkanol. However, the disadvantage of the procedure of German Patent 2,552,987 is that, in spite of a distillative treatment of the discharge from the reaction mixture and recycling of the resulting distillate to the reaction zone, the alkyl acrylate yield, based on acrylic acid used, is unsatisfactory. Furthermore, the residence time required in the embodiments is also unsatisfactory. The same applies to the space-time yield.

Continuous discharge of some of the reaction mixture is therefore required because, in the course of the esterification, even in the presence of polymerization inhibitors preferably concomitantly used in an amount known per se (for example, phenolic compounds, such as hydroquinone or hydroquinone monomethyl ether, or p-benzophenone, phenothiazine, methylene blue, phenyl enediamine and/or air), the α,β-monoethylenically unsaturated compounds involved form a certain amount of oligomers and polymers (high boilers), whose accumulation in the reaction zone it is intended to prevent.

It is an object of the present invention to provide a process for the continuous preparation of alkyl esters of (meth)acrylic acid by reacting (meth)acrylic acid and monohydric alkanols of 1 to 8 carbon atoms in a homogeneous, liquid, solvent-free phase, which process does not have the disadvantages of the processes of the most closely related art, ie. in particular no longer requires working up of the discharge from the reaction zone by distillation, and, with a simultaneously reduced residence time of the reactants in the reaction zone, nevertheless gives a high alkyl (meth)acrylate yield, based on acrylic acid used, without the formation of significantly more dialkyl ethers of the starting alkanol.

We have found that this object is achieved by a process for the continuous preparation of alkyl esters of (meth) acrylic acid by reacting (meth)acrylic acid and a monohydric alkanol of 1 to 8 carbon atoms in a homongeneous, liquid, solvent-free phase in a molar ratio of from 1 (alkanol):1 ((meth)acrylic acid) to 2 (alkanol):1 ((meth)acrylic acid) at elevated temperatures and in the presence of sulfuric acid or of an organic sulfonic acid as catalyst, in which the (meth)acrylic acid, the alkanol and the acid catalyst are fed continuously to a reaction zone, after a residence time of a few hours the resulting alkyl (meth)acrylate is separated off by rectification, as part of at least one azeotropic mixture consisting of water or water and starting alkanol as further components in addition to the alkyl (meth)acrylate, via the top of a rectification zone attached to the reaction zone and having a top pressure of from 0.1 to 1 atm, the distillate obtained is separated into at least one organic phase containing the alkyl (meth)acrylate and into at least one aqueous phase containing water, some of said organic phase is recycled to the rectification zone via the top and, if required, water is recycled to the reaction zone, the alkyl (meth)acrylate is separated off in a manner known per se from the excess organic phase containing the alkyl (meth)acrylate and some of the reaction mixture is discharged continuously from the reaction zone, wherein the reaction temperature is from 100° to 150° C.,
the residence time is from 1 to 5 hours and
the reaction mixture present in the reaction zone contains, as an added acid catalyst, from 5 to 20% by weight, based on the amount of reaction mixture, of sulfuric acid or an equimolar amount, based on such an amount of sulfuric acid, of an organic sulfonic acid or an equimolar amount, based on such an amount of sulfuric acid, of a mixture of sulfuric acid and organic sulfonic acid.

Preferably from 5 to 15, particularly preferably from 5 to 10%, by weight, based on the amount of reaction mixture, of sulfuric acid or an equimolar amount, based on such an amount of sulfuric acid, of an organic sulfonic acid or an equimolar amount, based on such an amount of sulfuric acid, of a mixture of sulfuric acid and organic sulfonic acid is added to the reaction mixture present in the reaction zone. The lower limit of the abovementioned ranges of the amounts of the acid added as a catalyst is advantageously 5.5, particularly advantageously 6, particularly preferably >8% by weight. Particularly advantageous catalytically active organic sulfonic acids are methanesulfonic acid, benzenesulfonic acid, dodecylbenzenesulfonic acid and p-toluene-sulfonic acid.

The reaction temperature is preferably from >100° to 140° C., particularly advantageously from 120° to 130° C. The residence time in the reaction zone is preferably from 2 to <4, particularly advantageously from 3 to <4, hours. The starting alkanol and the starting acid are advantageously fed to the reaction zone in a molar ratio of from 1.3:1 to 1.7:1. Furthermore, the top pressure of the rectification zone is advantageously 1 atm. A preferred starting acid is acrylic acid. In addition to 2-ethylhexanol, particularly useful starting alkanols for the novel process are the alkanols of 1 to 4 carbon atoms. Among the latter, methanol, ethanol, n-propanol, isopropanol, n-butanol, isobutanol and secbutanol are particularly suitable. The novel process is particularly useful for the preparation of n-butyl acrylate, and all statements herein therefore relate in particular to the esterification of n-butanol with acrylic acid.

With regard to working up the aqueous azeotropic mixture containing the target ester and separated off continuously from the reaction zone via the top of a rectification zone in the novel process, the distinction may be made essentially between two cases. If a heteroazeotropic mixture is obtained, as, for example, in the case of the novel preparation of n-butyl acrylate, the azeotropic mixture, after its condensation, separates by itself into an aqueous and into an organic phase. The aqueous phase usually comprises mainly water and a little alkanol while the organic phase generally essentially comprises the ester formed and the alkanol. To establish the separation effect by rectification, an appropriate part of the organic phase is recycled via the top to the rectification zone.

To maintain the composition of the aqueous azeotropic mixture, an appropriate part of the aqueous phase is recycled to the reaction zone, preferably likewise via the top of the attached rectification zone. Alkanol present can be separated, for example by stripping (eg. with air), from that portion of the aqueous phase which is not recycled, and can be recycled to the reaction zone. Advantageously, recycling is effected directly. The resulting essentially pure water is discharged. The resulting alkyl (meth)acrylate is separated from that part of the organic phase which is not recycled, separation being effected in a manner known per se, for example according to DE-A 2552987, i.e., for example, the excess organic phase is fed to a downstream first rectification column and the alkanol is separated off via the top in pure form or as an azeotropic mixture consisting of ester and alkanol. The alkanol thus separated off (in pure or in azeotropic form) is preferably recycled to the reaction zone. Recycling is advantageously effected directly. The bottom liquid of this first rectification column essentially comprises the desired ester and small amounts of byproducts having lower and higher boiling points than this ester. The bottom liquid of the first rectification column is therefore also referred to as crude alkyl (meth)acrylate. The lower-boiling byproducts are in particular the dialkyl ether and the acetate of the starting alkanol, since the esterification of (meth) acrylic acid with alkanols is usually carried out starting from crude (meth)acrylic acid. This is produced predominantly by catalytic gas-phase oxidation of $C_3/C_4$ starting compounds, such as propene or isobutene, minor amounts of acetic acid being formed as a byproduct (cf. for example DE-A 4436243). Higher-boiling byproducts are, for example, oligomers and polymers of the α,β-monoethylenically unsaturated target ester. In a downstream low boiler rectification column, the low-boiling byproducts are separated from the crude alkyl (meth)acrylate, usually via the top, before the desired pure alkyl (meth)acrylate can be isolated via the top in a high boiler rectification column downstream of said low boiler rectification column. The bottom liquid obtained from the high boiler rectification column and containing the high-boiling byproducts is advantageously recycled to the reaction zone, preferably directly. To maintain a steady state, a small amount of reaction mixture is continuously discharged from said reaction zone in order to avoid accumulation of high boilers there. The amount of acid catalyst discharged therewith is replenished in the reaction zone. If the aqueous azeotropic mixture containing the target ester and separated off continuously from the reaction zone via the top of a rectification zone in the novel process is not a heteroazeotropic mixture, it does not separate by itself into an aqueous and into an organic phase after its condensation. This separation can, however, be brought about in a simple manner, for example by extracting the alkanol present in the azeotropic mixture by means of water and separating the resulting water/alkanol mixture by rectification. The alkanol is advantageously recycled to the reaction zone, preferably directly. Water is, if required, recycled to the reaction zone, preferably via the top of the attached rectification zone. The organic phase obtained in the separation of the alkanol by extraction contains the target ester. Some of this is therefore recycled via the top of the attached rectification column for establishing the separation effected based on rectification. The target ester can be isolated from the excess organic phase in a manner known per se (for example as described above). Alkanol obtained in the procedure is advantageously recycled to the reaction zone, preferably directly. Usually, the aqueous azeotropic mixture removed from the reaction zone contains no starting acid when the separation effect based on rectification is correctly established. If this is not the case, however, said starting acid can be separated off together with the alkanol by extraction with water, and the extract then separated by rectification in a manner known per se. Of course, both the esterification reaction and the separations by rectification and extractions are carried out in the novel process preferably in the presence of the usual amounts of conventional polymerization inhibitors. As a rule, from 0.01 to 0.1% by weight, based on the amount of the α,β-monoethylenically unsaturated monomers, of a suitable polymerization inhibitor is used. Examples of suitable polymerization inhibitors are phenolic compounds, such as hydroquinone and hydroquinone monomethyl ether, and p-benzoquinone, phenothiazine, methylene blue, phenylenediamines and/or air.

Compared with the prior art processes, the novel process is distinguished by shorter residence times, a higher yield, based on starting acid used, of desired ester, reduced discharge from the reaction zone and the fact that it is no longer necessary to work up the continuous discharge from the reaction zone. Both the latter and the increased yield are presumably due to the fact that the steady state established in the reaction zone is kinetically controlled. The recleavage of relatively high-boiling oxyesters (for example alkoxypropionates or acyloxypropionates) probably plays a key role here. These compounds are formed, for example, by a Michael addition reaction between unconverted starting acid or starting alkanol and alkyl (meth)acrylate already formed:

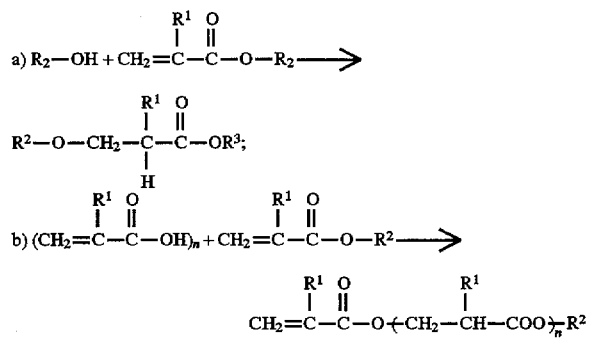

where $R^1$ is hydrogen or —$CH_3$,
$R^2$ is $C_1$–$C_8$-alkyl and
n is an integer.

In particular, the greater amount of catalytically active acid used in the novel process, together with a higher reaction temperature, evidently promotes the cleavage of the oxyesters back into their starting compounds and thus ensures a steady state particularly low in oxyesters in the reaction zone. Similarly, the oxyesters containing chemically bonded starting material and desired product are present in the discharge from the reaction zone only in such a small amount that working up of the discharge is no longer essential. If, however, starting material and desired product are removed from the reaction system to a smaller extent as a result of reduced oxyester formation, the yield based on starting material must inevitably increase. It is surprising that the significant improvement in yield which is achieved according to the invention does not necessarily result in a significant increase in dialkyl ether formation.

EXAMPLES (STABILIZATION WAS EFFECTED WITH PHENOTHIAZINE IN ALL CASES)

4 mol/h of acrylic acid, 4 mol/h of fresh n-butanol and 2 mol/h of n-butanol from the butanol recovery were fed continuously to a forced-circulation reboiler (empty volume 2.5, 1 capacity 2 l) as a reaction zone (residence time=2.3 hours). The esterification temperature was brought to 126° C. The acid catalyst used was sulfuric acid. The amount of sulfuric acid added to the reaction zone was brought to a steady-state value of X % by weight, based on the amount of reaction mixture present in said reaction zone. The forced-circulation reboiler was connected to a bubble-tray column (30 trays, 50 mm diameter) as an attached rectification zone, via the top of which (top pressure =1 atm) n-butyl acrylate formed was removed continuously as a component of a heteroazeotropic mixture additionally containing n-butanol and water. After condensation, the heteroazeotropic distillate separated into an organic and an aqueous phase. 350 ml/h of the aqueous phase and 180 ml/h of the organic phase were recycled via the top of the bubble-tray column. The excess organic phase (620 ml/h) was fed continuously to the middle section of a second corresponding downstream bubble-tray column. In this n-butanol recovery column, the n-butanol present in the organic phase was separated off via the top, together with residual water likewise present therein and with some of the n-butyl acrylate (278 ml/h in condensed form, including 83% by weight of n-butanol), and recycled directly to the reaction zone. The top pressure of the second bubble-tray column was 0.6 atm. The bottom product of the n-butanol recovery column (bottom temperature=130° C.) contained crude n-butyl acrylate having a purity of 99.5% by weight. After low boilers and high boilers had been separated off by a downstream rectification, a pure n-butyl acrylate having a purity of $\geq$99.95% by weight was obtained. The bottom liquid of the high boiler column was recycled in an amount of 30 g/h directly to the reaction zone. Y g/h of reaction mixture were discharged continuously from the reaction zone during the process. The table below shows the n-butyl acrylate yields A, based on acrylic acid used (% of theoretical achievable yield), achieved for various steady-state sulfuric acid contents X in the reaction zone. The data are based on the amount of n-butyl acrylate contained in the crude n-butyl acrylate. Furthermore, the table shows the amount of dialkyl ether contained in the crude n-butyl acrylate (% by weight, based on n-butyl acrylate contained in the crude n-butyl acrylate). The table also shows the required amount of discharge from the reaction zone (first as an absolute amount in g/h and secondly based on the amount of n-butyl acrylate in % by weight contained in the crude n-butyl acrylate).

Example V3 relates to a reaction temperature of 100° C. and Example V4 to a reaction temperature of 93° C. Correspondingly, the top pressure of the rectification zone attached to the reaction zone was 0.15 and 0.135 atm in these examples.

TABLE

| Example | X (% by weight) | A (% of theory) | Ether (% by weight) | Discharge [g/h] | Discharge based on n-BA (% by weight) |
|---|---|---|---|---|---|
| V1 | 3.0 | 96.8 | 0.043 | 14.2 | 2.9 |
| V2 | 4.5 | 97.1 | 0.077 | 11.3 | 2.3 |
| B1 | 6.3 | 97.6 | 0.090 | 9.0 | 1.8 |
| B2 | 9.3 | 98.7 | 0.132 | 2.5 | 0.5 |
| B3 | 14.4 | 99.0 | 0.178 | 2.3 | 0.5 |
| B4 | 18.6 | 99.3 | 0.190 | 2.0 | 0.4 |
| V3 | 3.0 | 94.3 | 0.002 | 25.1 | 5.2 |
| V4 | 3.0 | 91.9 | 0.001 | 29.6 | 6.3 |

We claim:

1. A process for the continuous preparation of alkyl esters of (meth)acrylic acid by reacting (meth)acrylic acid and a monohydric alkanol of 1 to 8 carbon atoms in a homogeneous, liquid, solvent-free phase in a molar ratio of from 1 (alkanol):1 ((meth)acrylic acid) to 2 (alkanol):1 ((meth)acrylic acid) at elevated temperatures and in the presence of sulfuric acid or of an organic sulfonic acid as catalyst, in which the (meth)acrylic acid, the alkanol and the acid catalyst are fed continuously to a reaction zone, after a residence time of a few hours the resulting alkyl (meth)acrylate is separated off by rectification, as part of at least one azeotropic mixture consisting of water or water and starting alkanol as further components in addition to the alkyl (meth)acrylate, via the top of a rectification zone attached to the reaction zone and having a top pressure of from 0.1 to 1 atm, the distillate obtained is separated into at least one organic phase containing the alkyl (meth)acrylate and into at least one aqueous phase containing water, some of said organic phase is recycled to the rectification zone via the top and, if required, water is recycled to the reaction zone, the alkyl (meth)acrylate is separated off in a manner known per se from the excess organic phase containing the alkyl (meth)acrylate and some of the reaction mixture is discharged continuously from the reaction zone, wherein the reaction temperature is from 100° to 150° C., the residence time is from 1 to 5 hours and the reaction mixture present in the reaction zone contains, as an added acid catalyst, from 5 to 20% by weight, based on the amount of reaction mixture, of sulfuric acid or an equimolar amount, based on such an amount of sulfuric acid, of an organic sulfonic acid or an equimolar amount, based on such an amount of sulfuric acid, of a mixture of sulfuric acid and organic sulfonic acid.

2. A process as claimed in claim 1, wherein the amount of acid catalyst added to the reaction mixture consists of from 5 to 15% by weight, based on the amount of reaction mixture, of sulfuric acid, of an equimolar amount, based on such an amount of sulfuric acid, of an organic sulfonic acid or of an equimolar amount, based on such an amount of sulfuric acid, of a mixture of sulfuric acid and organic sulfonic acid.

3. A process as claimed in claim 1, wherein the amount of acid catalyst added to the reaction mixture consists of from 5 to 10% by weight, based on the amount of reaction mixture, of sulfuric acid, of an equimolar amount, based on such an amount of sulfuric acid, of an organic sulfonic acid or of an equimolar amount, based on such an amount of sulfuric acid, of a mixture of sulfuric acid and organic sulfonic acid.

4. A process as claimed in claim 1, wherein the lower limit of the range of the amounts of added acid catalyst is 5.5% by weight.

5. A process as claimed in claim 1, wherein the lower limit of the range of the amounts of added acid catalyst is 6% by weight.

6. A process as claimed in claim 1, wherein the lower limit of the range of the amounts of added acid catalyst is >8% by weight.

7. A process as claimed in claim 1, wherein the added acid catalyst comprises methanesulfonic acid, benzenesulfonic acid, dodecylbenzenesulfonic acid or p-toluenesulfonic acid.

8. A process as claimed in claim 1, wherein the reaction temperature is from >100° to 140° C.

9. A process as claimed in claim 1, wherein the reaction temperature is from 120° to 130° C.

10. A process as claimed in claim 1, wherein the residence time in the reaction zone is from 2 to <4 hours.

11. A process as claimed in claim 1, wherein the residence time in the reaction zone is from 3 to <4 hours.

12. A process as claimed in claim 1, wherein the starting alkanol and the starting acid are fed to the reaction zone in a molar ratio of from 1.3:1 to 1.7:1.

13. A process as claimed in claim 1, wherein the top pressure of the rectification zone attached to the reaction zone is 1 atm.

14. A process as claimed in claim 1, wherein the acid to be esterified is acrylic acid.

15. A process as claimed in claims 1, wherein the alkanol to be esterified is a $C_1$–$C_4$-alkanol.

16. A process as claimed in claim 1, wherein the alkanol to be esterified is n-butanol.

* * * * *